(12) United States Patent
Abiri et al.

(10) Patent No.: US 9,523,639 B2
(45) Date of Patent: Dec. 20, 2016

(54) INTEGRATED WIDE TARGET RANGE OPTICAL COUPLING-BASED MACH-ZEHNDER SENSOR

(71) Applicant: California Institute of Technology, Pasadena, CA (US)

(72) Inventors: Behrooz Abiri, Pasadena, CA (US); Firooz Aflatouni, Philadelphia, PA (US); Seyed Ali Hajimiri, La Canada, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/690,190

(22) Filed: Apr. 17, 2015

(65) Prior Publication Data

US 2016/0097715 A1    Apr. 7, 2016

Related U.S. Application Data

(60) Provisional application No. 61/982,452, filed on Apr. 22, 2014.

(51) Int. Cl.
| | |
|---|---|
| *G01N 21/00* | (2006.01) |
| *C12Q 1/68* | (2006.01) |
| *G02B 6/26* | (2006.01) |
| *G01N 21/45* | (2006.01) |

(52) U.S. Cl.
CPC ......... *G01N 21/45* (2013.01); *G01N 2021/458* (2013.01); *G01N 2201/08* (2013.01)

(58) Field of Classification Search
CPC ............ G01N 21/00; C12Q 1/68; G02B 6/26; G02B 6/12; G02B 6/42
USPC ............... 422/50, 400, 68.1, 82.05, 82.06, 82.09,422/82.11, 91; 356/504, 477, 481, 517; 436/86, 436/164, 165, 171, 172; 385/14, 15, 31, 32, 39
See application file for complete search history.

(56) References Cited

U.S. PATENT DOCUMENTS

| | | | | |
|---|---|---|---|---|
| 5,405,583 | A * | 4/1995 | Goswami et al. | 422/86 |
| 7,016,094 | B2 * | 3/2006 | Awaya et al. | 359/245 |
| 7,023,601 | B2 * | 4/2006 | McGhan et al. | 359/246 |
| 2003/0118279 | A1 * | 6/2003 | Izhaki et al. | 385/21 |
| 2003/0174743 | A1 * | 9/2003 | Cliche et al. | 372/20 |
| 2004/0151423 | A1 * | 8/2004 | Izhaky et al. | 385/21 |
| 2004/0179764 | A1 * | 9/2004 | Melikechi et al. | 385/1 |
| 2004/0179781 | A1 * | 9/2004 | Melikechi et al. | 385/39 |
| 2005/0271327 | A1 * | 12/2005 | Burie et al. | 385/43 |

* cited by examiner

*Primary Examiner* — Brian J Sines
(74) *Attorney, Agent, or Firm* — Alston & Bird LLP

(57) ABSTRACT

A sensor includes, in part, a multitude of splitters/couplers and optical couplers. One of the splitter/couplers splits an incoming optical signal into first and second optical signals. A first optical coupler includes, in part, a through path receiving the first signal, a coupled path, and an exposure window receiving a sample undergoing sensing by the sensor. The second optical coupler includes, in part, a through path receiving the second signal, and a coupled path. A first output port of the sensor supplies the optical signal travelling in the through path of the first optical coupler. A second splitter/coupler combines the optical signals travelling in the coupled paths of the first and second optical couplers to generate a second output signal delivered to a second output port. An optional third output port supplies the optical signal travelling in the through path of the second optical coupler.

10 Claims, 3 Drawing Sheets

INTEGRATED WIDE TARGET RANGE OPTICAL COUPLING-BASED MACH-ZEHNDER SENSOR

CROSS-REFERENCES TO RELATED APPLICATIONS

The present application claims benefit under 35 USC 119 (e) of U.S. provisional Application No. 61/982,452, filed Apr. 22, 2014, entitled "INTEGRATED WIDE TARGET RANGE OPTICAL COUPLING-BASED MACH-ZEHNDER SENSOR", the content of which is incorporated herein by reference in its entirety.

BACKGROUND OF THE INVENTION

The present application relates to measuring the refractive index of a sample using optical sensing.

Solid state Mach-Zehnder Interferometers (MZI) have been used in measuring the refractive index of a medium, sensing of label-free bio-chemical materials and DNA hybridization. FIG. 1 is a simplified schematic diagram of a MZI-based sensor 10 having an input port 10 and an output port 20, as known in the prior art. The optical signal received at input port 10 is split into two beams via splitter/coupler 35 and caused to travel in optical paths 15 and 20 formed using, for example, silicon waveguides. Optical path 15 includes a window 30 adapted to hold a sample of the material or compound (hereinafter alternatively referred to as sample) whose refractive index, or changes in its refractive index due to a chemical reaction, is being measured. No such window is present in optical path 25. The optical signals travelling in paths 15 and 25 are combined by splitter/coupler 40 and supplied at output port 20. If the optical signals arriving at splitter/coupler 40 have the same phase, they add constructively to form a maxima. Conversely, if the optical signals arriving at splitter/coupler 40, 20 are 180° out-of-phase, they thus cancel out each other. Other relative phase differences result in other values of the optical signal power at output port 20 of MZI-based sensor 10.

The difference between the phases of the two optical signals arriving at splitter/coupler 40—and therefore the power of the optical signal at output port (hereinafter alternatively referred to as the output signal) 20—is dependent on the refractive index of the sample disposed in window 30 as well as the length L of window 30.

In order to increase the sensitivity of an MZI-based sensor (alternatively referred to herein as sensor), the dependency of the effective refractive index of the waveguide to the sample's refractive index needs to increase. To achieve this, in some conventional MZI-based sensors, the ratio of the evanescent component of the electromagnetic (EM) field to the propagating component of the EM field is increased by either reducing the size of the waveguide core, or reducing the refractive index contrast of the waveguide to that of the material enclosing the waveguide. In silicon photonics, the high refractive index of a Silicon waveguide relative to the refractive index of the medium, such as Silicon dioxide, enclosing the waveguide results in a small ratio of the evanescent field component relative to the propagating field component, thereby causing the sensitivity of the sensor for a given exposure window length to decrease.

Another shortcoming of a conventional MZI-based sensor is the inverse relationship between its sensitivity and the range of refractive indices it is able to sense. This is due to the fact that the response of a conventional MZI-based sensor to two optical signals that have a phase difference of $\phi$ and $(2m\pi+\phi)$, where in is an integer, is the same. Accordingly, unless the approximate refractive index of the sample is known to within a narrow range, conventional MZI-based sensors are unable to uniquely determine a sample's refractive index.

FIG. 2 is a simplified schematic diagram of an MZI-based sensor 200, as is also known in the prior art. MZI-based sensor 200 includes an input port 210 and a pair of output ports 280 and 290. The optical signal received at input port 210 is split into two beams travelling in optical waveguides (paths) 215 and 225. Optical waveguide 215 is split into two equal paths 230 and 235 at splitter/coupler 218, and optical waveguide 225 is split into two equal paths 240 and 245 at splitter/coupler 338. Optical waveguides 230 and 235 are combined by splitter/coupler 228 leading to an output port 228. Likewise, optical waveguides 240 and 245 are combined by splitter/coupler 248 leading to an output port 248. Waveguides 230 and 240 respectively include exposure windows 260 and 270 adapted to include a sample whose index of refraction is being measured. Window 260 is longer and is thus more sensitive than window 270 but has a smaller one-to-one index range than window 270.

Since exposure windows 260 and 270 are spatially separated, the samples dispensed therein may not be sensed similarly if, for example, there is a gradient in the index of refraction of the sample solution. Also, the two exposure windows 200 and 270 may provide different chemical reaction rates.

BRIEF SUMMARY OF THE INVENTION

A sensor, in accordance with one embodiment of the present invention, includes, in part, at least a pair of splitters/couplers, at least a pair of optical couplers, and at least a pair of output ports. A first splitter/coupler is adapted to split an incoming optical signal into first and second optical signals. A first optical coupler includes a through path, a coupled path, and an exposure window adapted to receive a sample. The first optical signal enters the first optical coupler via the through path of the first optical coupler. A second optical coupler includes a through path and a coupled path. The second optical signal enters the second optical coupler via the through path of the second optical coupler. A first output port supplies a first output signal from the first through path of the first optical coupler. A second splitter/coupler combines the optical signals travelling through the coupled paths of the first and second optical couplers to generate a second output signal supplied via the second output port.

In one embodiment, the sensor includes a third output port supplying a third output signal from the first through path of the second optical coupler. In one embodiment, the through and coupled paths of each of the first and second optical couplers are waveguides. In one embodiment, the through and coupled paths of the second optical coupler are enclosed in a dielectric.

In one embodiment, the waveguides of each of the first and second optical coupler are formed using Silicon and the waveguides of the second optical coupler are enclosed in Silicon Dioxide. In one embodiment, the sample includes a protein molecule. In another embodiment, the sample includes a DNA molecule. In yet another embodiment, the sample includes a nucleic-acid molecule. In one embodiment, the sensor senses a chemical reaction rate on the sample. In one embodiment, the sensor senses the pressure or humidity of air.

A method of determining an index of refraction of a sample includes, in part, splitting an incoming optical signal into first and second optical signals, delivering the first optical signal to a first optical coupler that includes, in part, a through path and a coupled path. The first optical signal enters the first optical coupler via the through path of the first optical coupler. The method further includes, in part, placing the sample in an exposure window of the first optical coupler, delivering the second optical signal to a second optical coupler that includes, in part, a through path and a coupled path. The second optical signal enters the second optical coupler via the through path of the second optical coupler. The method further includes, in part, supplying a first output signal from the first through path of the first optical coupler, combining the optical signals travelling through the coupled paths of the first and second optical couplers to generate a second output signal, and determining the index of refraction of the sample using the first and second output signals.

The method, in accordance with one embodiment, further includes, in part, supplying a third output signal from the first through path of the second optical coupler. In one embodiment, the through and coupled paths of each of the first and second optical couplers are waveguides. In one embodiment, the through and coupled paths of the second optical coupler are enclosed in a dielectric.

In one embodiment, the waveguides of each of the first and second optical coupler are formed using Silicon and the waveguides of the second optical coupler are enclosed in Silicon Dioxide. In one embodiment, the sample includes a protein molecule. In another embodiment, the sample includes a DNA molecule. In yet another embodiment, the sample includes a nucleic-acid molecule. In one embodiment, the sensor senses a chemical reaction rate on the sample. In one embodiment, the sensor senses the pressure or humidity of air.

DETAILED DESCRIPTION OF THE INVENTION

A sensor includes, in part, an input port, a multitude of splitters/couplers, a multitude of output ports, and at least a pair of optical couplers. A first splitter/coupler splits an incoming optical signal received via the input port to generate first and second optical signals. The first optical coupler includes, in part, a through path receiving the first optical signal, a coupled path, and an exposure window adapted to receive a sample undergoing sensing and measurement by the sensor. The second optical coupler includes, in part, a through path receiving the second optical signal, and a coupled path. A first output port of the sensor supplies the optical signal travelling in the through path of the first optical coupler. A second splitter/coupler combines the optical signals travelling in the coupled paths of the first and second optical couplers to generate a second output signal that is delivered to a second output port of the sensor. A third and optional output port of the sensor supplies the optical signal travelling in the through path of the second optical coupler.

Figure 1:
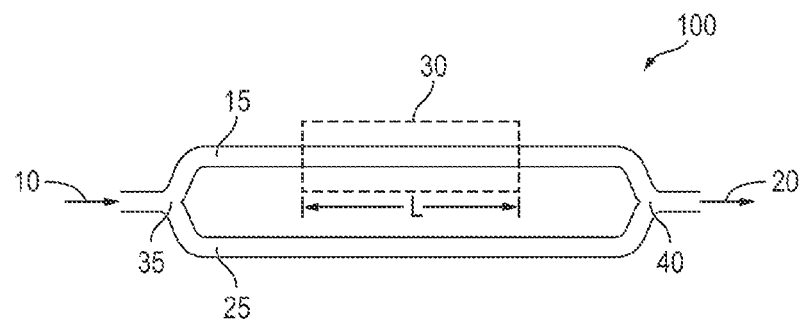
FIG. 1 is a simplified schematic diagram of a MZI-based sensor, as known in the prior art.
Figure 2:
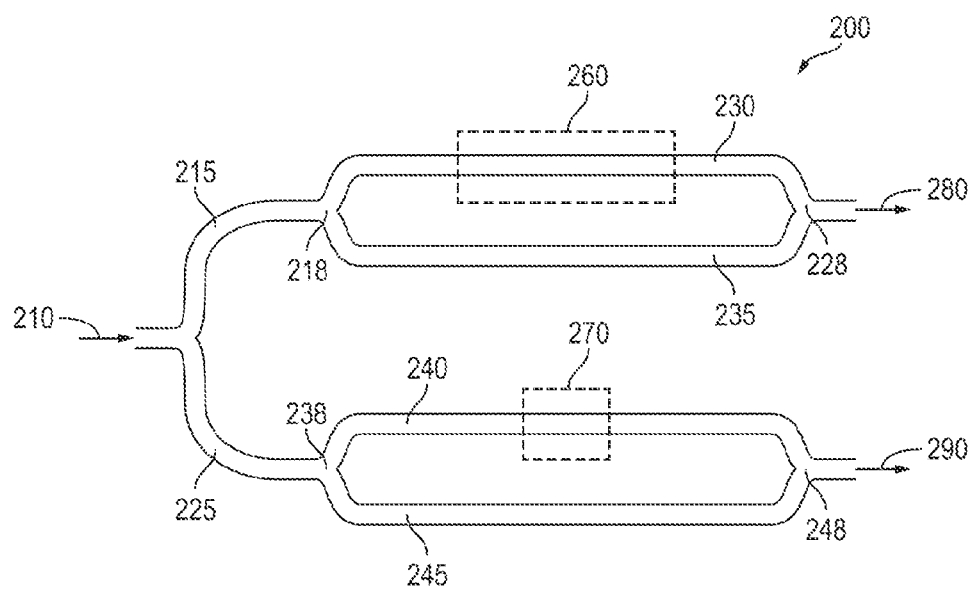
FIG. 2 is a simplified schematic diagram of a MZI-based sensor, as known in the prior art.
Figure 3:
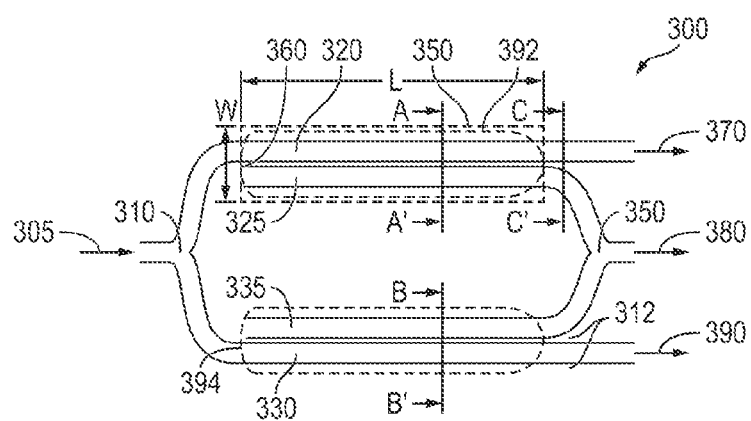
FIG. 3 is a simplified schematic diagram of a MZI-based sensor, in accordance with one embodiment of the present invention.

FIG. 3 is a simplified schematic diagram of a sensor 300, in accordance with one embodiment of the present invention, that operates based on the principles of the Mach-Zehnder interferometry to sense and determine the refractive index or change in the refractive of a sample. As described further below, sensor 300 generates a multitude of output signals to provide, among other things, a first measure of the refractive index having a relatively low sensitivity and a relatively wide index range, as well as a second measure of the refractive index having a relatively higher sensitivity and a relatively narrower index range. Sensor 300 is thus adapted to uniquely determine the index of refraction of a sample, or change in the index of refraction of a sample caused by a chemical reaction, over a relatively wide range. Sensor 300 may be used, for example, in the detection of protein molecules, DNA and other nucleic-acid molecules. Sensor 300 may also be used, for example, in sensing a chemical reaction rate, or in sensing the pressure of air whose index of refraction varies depending on its pressure, or in sensing the humidity, and the like. It is understood that sensor 300 may be used in many other sensing applications.

Sensor 300 is shown as including, in part, an input port 305, and three output ports 370, 380, and 390. Signal splitter/coupler 310 splits the optical signal received at input port 305 into two optical signals and delivers them to waveguides 320 and 330 which have equal lengths. Sensor 300 also includes, in part, waveguide 325 positioned adjacent waveguides 320 along a known length L of waveguide 320 to form a first optical coupler 392. Optical coupler 392 thus has a through waveguide or optical path 320 and a coupled waveguide or optical path 325. Sensor 300 further includes, in part, waveguide 335 positioned adjacent waveguides 330 along the length L of waveguide 330 (in the same manner as waveguide 325 is positioned adjacent waveguide 320) to form a second optical coupler 394. Optical coupler 394 thus has a through waveguide or optical path 330 and a coupled waveguide or optical path 335. As is seen from FIG. 3, sensor 300 has a symmetrical structure. Waveguides 325 and 335 are subsequently coupled to one another by signal splitter/coupler 350 to form an output port 380.

Figure 4A:
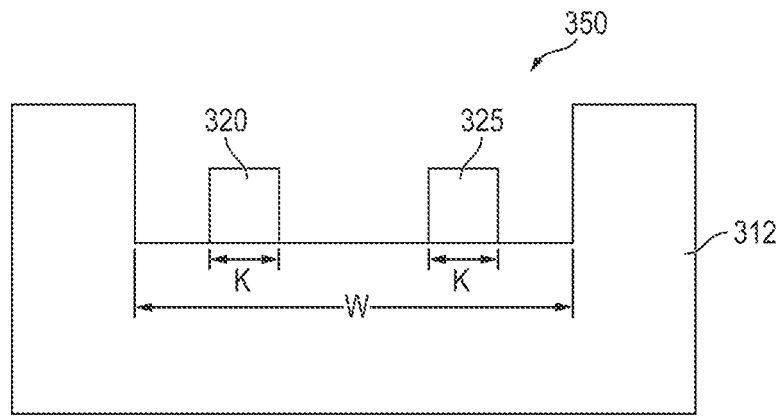
FIG. 4A is a cross-sectional view of the sensor shown in FIG. 3 along lines A-A' within the sensor's exposure window, in accordance with one embodiment of the present invention.

Sensor 300 includes an exposure window 350—formed along the length L of waveguides 320, 325—adapted to hold a sample of the material, compound or substance (collectively and alternatively herein referred to as sample) whose index of refraction is being measured by sensor 300. FIGS. 4A are 4B are cross-sectional views of sensor 300 along lines A-A' and B-B', respectively. Optical waveguides 320, 325, 330, 335 may be formed using any number of materials. As is seen from FIG. 4A, waveguides 320 and 325 in exposure window 350 are enclosed by air when no sample is present therein. Waveguides 320 and 325 are enclosed by a sample different than air when exposure window 350 is filled with that sample to enable the index of refraction of that sample to be measured. Sensor 300 may also be used to measure the change in the index of refraction of a sample present in exposure window 350 when the sample is caused to chemically react with a different sample added to exposure window 350.

Figure 4B:
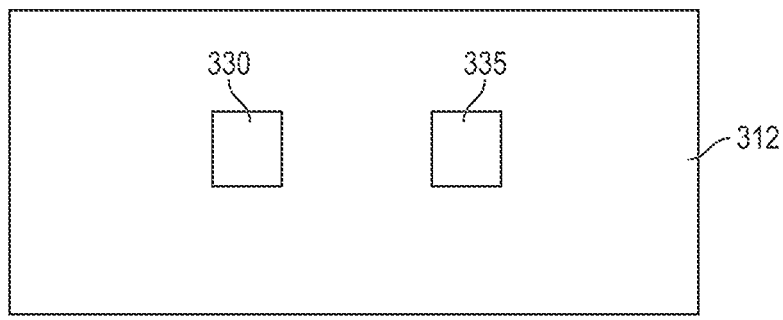
FIG. 4B is a cross-sectional view of the sensor shown in FIG. 3 along lines B-B', in accordance with one embodiment of the present invention.
Figure 4C:
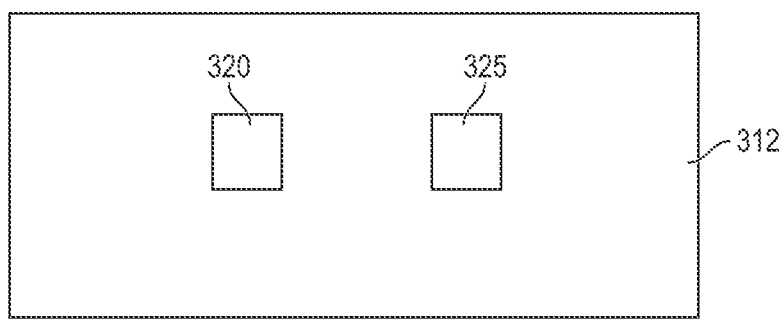
FIG. 4C is a cross-sectional view of the sensor shown in FIG. 3 along lines C-C' outside the sensor's exposure window, in accordance with one embodiment of the present invention.

FIG. 4C is a cross-sectional view of sensor 300 along line C-C' outside exposure window 350. Material 312 shown in FIGS. 4B and 4C as enclosing waveguides 320, 325, 330, and 335 may be formed using any number of materials, such as Silicon Dioxide. The following description of the exemplary embodiment of sensor 300 is provide with reference to optical waveguides 320, 325, 330, 335 as being Silicon waveguides formed in Silicon Dioxide 312. It is understood, however, that optical waveguides 320, 325, 330, 335 may be formed using any number of materials. Likewise, material 312 enclosing the waveguides may be formed using any number of materials.

The higher the index of refraction of a waveguide (e.g., waveguide 330) relative to that of the material enclosing the waveguide (e.g., material 312), the more confined is the optical beam within the waveguide, and thus the smaller is the component of the evanescent field within the material enclosing the waveguide. For example, since the index of refraction of Silicon is approximately 3.4, and the index of refraction of Silicon Dioxide is approximately 1.5, the light travelling through the Silicon waveguide 330 has a substantially higher field component along the propagation direction (i.e., the length of the waveguide) than then evanescent component penetrating the Silicon Dioxide 312 enclosing waveguide 330.

Because waveguides 320 and 325 are positioned adjacent one another to form optical coupler 392, the evanescent field component of the optical beam in waveguide 320 is coupled to waveguide 325. Likewise, because waveguides 330 and 335 are positioned adjacent one another to form optical coupler 394, the evanescent field component of the optical beam in waveguide 330 is coupled to waveguide 335. The higher is the index of refraction of waveguide 320 compared to the index of refraction of the material separating waveguide 320 from waveguide 325 (i.e., the sample disposed in exposure window 350), the smaller is the degree of optical coupling between waveguides 320 and 325.

Figure 5A:
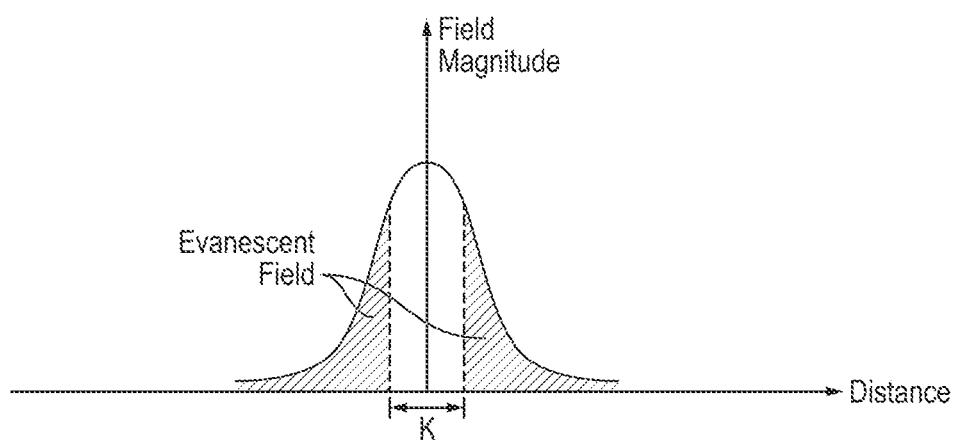
FIGS. 5A and 5B are examples of the field distribution within one of the optical waveguides of the sensor shown in FIG. 3 before and after placing a sample in the exposure window of the sensor, in accordance with one embodiment of the present invention.
Figure 5B:
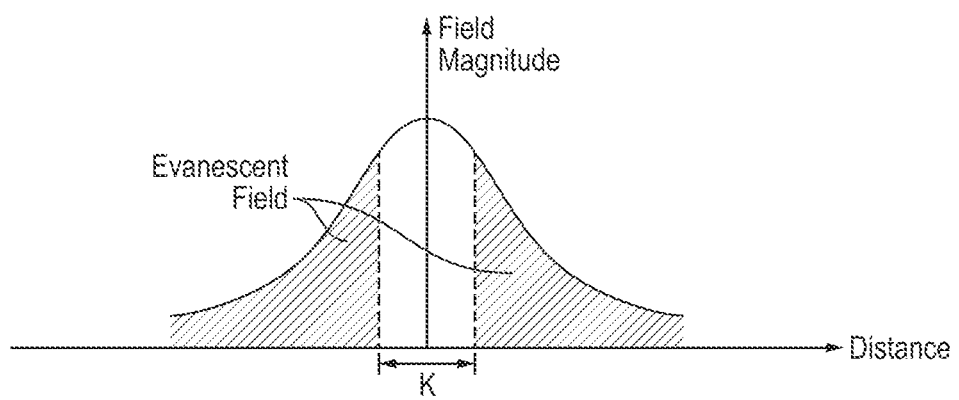

When no sample is present in exposure window 350, waveguides 320 and 325 are separated by air which has a refractive index of 1. Since the index of refraction of any sample is higher than 1, the degree of optical coupling between waveguides 320 and 325 increases when a sample is placed in exposure window 350. FIGS. 5A and 5B respectively show examples of the field distribution within optical waveguide 320 before and after placing a sample in exposure wind 350. As is seen by comparing FIGS. 5A and 5B, the higher index of refraction of the sample placed in exposure window 350 causes the optical field to widen and thus penetrate deeper into the sample, in turn causing the evanescent field component and thus the degree of coupling between waveguide 325 and 320 to increase.

Referring to FIG. 3, the light entering sensor 300 at input port 305 is split into two beams by splitter/coupler 310. The light entering the through waveguide 320 of optical coupler 390 is partly coupled to coupled waveguide 325 of optical coupler 392 and subsequently exits sensor 300 at output port 370 where it is measured. The light (optical signal) entering through waveguide 330 of optical coupler 394 is partly coupled to coupled waveguide 335 of optical coupler 394 and subsequently exits sensor 300 at output port 390 where it is measured. The optical signals coupled to waveguides 325 and 335 are combined by splitter/coupler 350 before exiting sensor 300 at output port 380 where it is measured. Although not shown for clarity, in one embodiment, the optical signal power exiting any one of the output ports may be measured by one or more photo-detectors such as photo-diodes. In one embodiment, such photo-diodes are formed in the same substrate in which sensor 300 is integrated. In yet other embodiments, one or more bolometers may be used to measure the power of the optical signals at the output ports of sensor 300. In one embodiment, sensor 300 is integrated in a substrate, such as Silicon substrate.

When two single mode optical waveguides, such as waveguides 320 and 325, are brought close to one another, the light travelling in one waveguide starts to couple to the other waveguide. Such coupling may be explained by treating the two waveguides as a single waveguide structure and finding the optical modes corresponding to that waveguide structure. Such a waveguide structure supports two optical modes, namely a symmetric mode and an anti-symmetric mode. These two modes are orthogonal to each other, and have slightly different propagation speed, and therefore different effective indices of refraction.

When light enters one of the waveguides of an optical coupler, the optical field is present only in that waveguide at the point of entry. As the light propagates through the waveguide, the phase of the two optical modes begins to vary. Since the propagation speeds of the two optical modes (symmetric and anti-symmetric modes) are different, a phase mismatch appears between the two optical modes, thereby resulting in change in the distribution of optical power in the coupler. In other words, the light starts to move from one waveguide of the optical coupler to the other waveguide of the optical coupler.

Referring to FIG. 3, the electric field in through waveguide 320 and 330, namely $E_T$, may be defined as follow:

$$E_T(t, x) = \frac{1}{2}e^{-i\omega t + i\frac{2\pi n_s}{\lambda}x} + \frac{1}{2}e^{-i\omega t + i\frac{2\pi n_a}{\lambda}x} \quad (1)$$

The electric field in coupled waveguides 325 and 335, namely $E_C$, may be defined as:

$$E_C(t, x) = \frac{1}{2}e^{-i\omega t + i\frac{2\pi n_s}{\lambda}x} - \frac{1}{2}e^{-i\omega t + i\frac{2\pi n_a}{\lambda}x} \quad (2)$$

In expressions (1) and (2), $\lambda$ is the free space wavelength of the light, and $n_s$ and $n_a$ are respectively the effective index of refraction of the symmetric and anti-symmetric optical modes propagating through the optical couplers 392 and 394. As it is seen from these two equations, $E_T(t, 0) = \exp(i\omega t)$ and $E_C(t, 0) = 0$. In other words, at x=0 (e.g., point 360 in waveguide 320), the light is only present in the through waveguides 320, 330.

Expression (1) and (2) may be simplified respectively as shown below in expressions (3) and (4):

$$E_T(t, x) = e^{-i\omega t + i\frac{2\pi n}{\lambda}x}\cos\frac{\pi \Delta n}{\lambda}x \quad (3)$$

$$E_C(t, x) = e^{-i\omega t + i\frac{2\pi n}{\lambda}x}\sin\frac{\pi \Delta n}{\lambda}x \quad (4)$$

where,

-continued $$n = (n_s + n_a)/2 \quad (5)$$

and $$\Delta n = n_s - n_a \quad (6)$$

The above expressions show the variations in $E_T$ and $E_C$ as the optical field propagates through the couplers. Assuming that each coupler has a length of L, the electric field at the output of each coupler may be expressed as:

$$E_T(t, L) = e^{-i\omega t + i\frac{2\pi n}{\lambda}L} \cos\frac{\pi\Delta n}{\lambda}L \quad (7)$$

$$E_C(t, L) = e^{-i\omega t + i\frac{2\pi n}{\lambda}L} \sin\frac{\pi\Delta n}{\lambda}L \quad (8)$$

In one embodiment, the optical signal exiting each of output ports 370, 380 and 390 may be measured by converting the optical signal to an electrical signal using, for example, a photo-diode (not shown in FIG. 3 for simplicity.) The output signal $OUT_1$ of a photo-diode receiving the light exiting output port 370 is proportional:

$$OUT_1 \alpha \cos^2 \frac{\pi \Delta n_e}{\lambda} L \quad (9)$$

where $\Delta n_e$ is the difference between the indices of refraction of the symmetrical and anti-symmetrical modes, as defined in expression (6) above, associated with the light travelling in optical coupler 392.

Likewise, the output signal $OUT_3$ of a photo-diode receiving the light exiting output port 390 is proportional to:

$$OUT_3 \alpha \cos^2 \frac{\pi \Delta n_r}{\lambda} L \quad (10)$$

where $\Delta n_r$ is the difference between the indices of refraction of the symmetrical and anti-symmetrical modes, as defined in expression (6) above, associated with the light travelling in the optical coupler 394.

The output signal $OUT_2$ of a photo-diode receiving the light exiting output port 380 is defined by the sum of the optical fields from waveguides 325, 335, and may be defined as being proportional to:

$$OUT_2 \alpha \cos^2 \frac{\pi(n_e - n_r)}{\lambda} L \quad (11)$$

where $n_e$ represents the average of $n_s$ and $n_a$ associated with optical coupler 392, and $n_r$ represents the average of $n_s$ and $n_a$ associated with optical coupler 394. It is seen that the signal at the outputs 370 and 380 are periodic with respect to $\Delta n_e$ and $n_e$ respectively, thereby providing a limited range of $n_e$ and $\Delta n_e$ for which the output of sensor 30 may be uniquely established.

Expressions (9) and (11) include two unknown parameters, namely $\Delta n_e$ and $n_e$, and thus can be solved concurrently to determine the values of these two parameters. Studies show that the change in $\Delta n_e$ due to the change in the material enclosing the optical couplers is smaller compared to the change in $n_e$. Therefore, output 370 has a wider one-to-one range but less sensitivity, while output 380 has a relatively higher sensitivity but a relatively lower detection range.

Assume that the silicon waveguides are formed from Silicon and the material enclosing the waveguides, other than in the exposure window 350, is formed from $SiO_2$. Further assume that the light has a wavelength $\lambda$ of 1550 nm. Assuming no sample is present in exposure window 350, i.e., exposure window 350 is exposed to air, in one example, $OUT_1$=0.00793, and $OUT_2$=1, thereby resulting in $\Delta n_e$=0.001462 and $n_e$=2.359689. In another example, if the exposure window includes water with a refractive index of 1.33, then $OUT_1$=0.98872 and $OUT_2$=0.5701, thereby resulting in $\Delta n_e$=0.002995 and $n_e$=2.4240835. In yet another example, if the exposure window includes salt water with a refractive index of 1.34, then $OUT_1$=0.9975 and $OUT_2$=0.0028, thereby resulting in $\Delta n_e$=0.003051 and $n_e$=2.4262865.

The above embodiments of the present invention are illustrative and not limitative. Embodiments of the present invention are not limited by the type of optical splitter/coupler, or waveguide used in the sensor. Embodiments of the present invention are not limited by the wavelength of the optical signal, the length of the exposure window in which a sample may be disposed, or the material enclosing the waveguides. Embodiments of the present invention are not limited by the type of substrate, semiconductor, flexible or otherwise, in which various components of a sensor in accordance with the present invention may be embodied. Other additions, subtractions or modifications are obvious in view of the present disclosure and are intended to fall within the scope of the appended claims.

What is claimed is:

1. A sensor comprising:
   a first splitter/coupler adapted to split an incoming optical signal into first and second optical signals;
   a first optical coupler comprising a through path and a coupled path, said first optical signal entering the first optical coupler via the through path of the first optical coupler, said first optical coupler comprising an exposure window adapted to receive a sample;
   a second optical coupler comprising a through path and a coupled path, said second optical signal entering the second optical coupler via the through path of the second optical coupler;
   a first output port supplying a first output signal from the first through path of the first optical coupler;
   a second splitter/coupler adapted to combine optical signals travelling through the coupled paths of the first and second optical couplers to generate a second output signal; and
   a second output port supplying the second output signal.

2. The sensor of claim 1 further comprising:
   a third output port supplying a third output signal from the first through path of the second optical coupler.

3. The sensor of claim 1 wherein said through and coupled paths of each of the first and second optical couplers are waveguides.

4. The sensor of claim 3 wherein said through and coupled paths of the second optical coupler are enclosed in a dielectric.

5. The sensor of claim 4 wherein the waveguides of each of the first and second optical coupler are formed using Silicon and wherein the waveguides of the second optical coupler are enclosed in Silicon Dioxide.

6. The sensor of claim 1 wherein said sample includes protein molecules.

7. The sensor of claim 1 wherein said sample includes DNA molecules.

8. The sensor of claim 1 wherein said sample includes nucleic-acid molecules.

9. The sensor of claim 1 wherein said sensor is adapted to sense a chemical reaction rate of the sample.

10. The sensor of claim 1 wherein said sensor is adapted to sense a pressure or humidity of air.

* * * * *